United States Patent
Schroeder et al.

(10) Patent No.: US 6,410,042 B1
(45) Date of Patent: Jun. 25, 2002

(54) PLANT PROTECTION PRODUCTS IN THE FORM OF A GRANULATE WITH CONTROLLED RELEASE OF THE ACTIVE AGENT

(75) Inventors: Manfred Schroeder, Neustadt; Reiner Kober, Fussgönheim; Reinhold Stadler, Kirrweiler; Jörn Tidow, Schwetzingen; Norbert Sendhoff, Grünstadt; Erich Probeck, Bockenheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/462,676

(22) PCT Filed: Jul. 2, 1998

(86) PCT No.: PCT/EP98/04095

§ 371 (c)(1),
(2), (4) Date: Jan. 11, 2000

(87) PCT Pub. No.: WO99/04634

PCT Pub. Date: Feb. 4, 1999

(30) Foreign Application Priority Data

Jul. 23, 1997 (DE) ......... 197 31 528

(51) Int. Cl.⁷ ............................................. A01N 25/12
(52) U.S. Cl. ............ 424/421; 424/405; 424/408; 424/409; 424/417; 424/421; 424/705; 504/101; 514/223.8

(58) Field of Search ............. 504/100, 101; 514/223.8, 514, 515; 424/405, 406, 408, 409, 417, 419, 421, 703, 705, 713, 704; 428/403; 71/64.02, 64.03, 64.07, 64.08, 64.13

(56) References Cited

U.S. PATENT DOCUMENTS

| | | | | |
|---|---|---|---|---|
| 2,519,891 A | * | 8/1950 | Dean et al. | 428/403 |
| 2,838,389 A | | 6/1958 | Yoder | |
| 5,495,017 A | | 2/1996 | Appler | |
| 5,703,103 A | * | 12/1997 | Heuer et al. | 514/365 |
| 5,712,304 A | * | 1/1998 | Elbe et al. | 514/272.4 |
| 5,760,067 A | * | 6/1998 | Jautelat et al. | 514/383 |
| 5,786,375 A | * | 7/1998 | Lindeman et al. | 514/383 |

FOREIGN PATENT DOCUMENTS

WO 93/13085 7/1993

OTHER PUBLICATIONS

Forest Products J., vol. 43, No. 2, 41–44, Forsyth et al. 2/93.
ActaHort 382, 1995, Dohmen et al., 110–118.
Wood and Fiber Sci., 27(2), 1995, 183–197, Forsyth et al.

* cited by examiner

Primary Examiner—Neil S. Levy
(74) Attorney, Agent, or Firm—Keil & Weinkauf

(57) ABSTRACT

Crop protection granules based on the active substance tetrahydro-3,5-dimethyl-1,3,5-thiadiazine-2-thione and comprising an outer shell having a proportion by weight of from 0.1 to 50% by weight, based on the granules, of which at least 50% by weight consists of sulfur or sulfur compounds.

9 Claims, No Drawings

PLANT PROTECTION PRODUCTS IN THE FORM OF A GRANULATE WITH CONTROLLED RELEASE OF THE ACTIVE AGENT

The present invention relates to crop protection granules based on the active substance tetrahydro-3,5-dimethyl-1,3,5-thiadiazine-2-thione.

U.S. Pat. No. 2,838,389 describes the use of tetrahydro-3,5-dimethyl-1,3,5-thiadiazine-2-thione of the formula (I), common name dazomet, as a soil decontaminant in agriculture and horticulture.

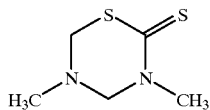
(I)

For an end user incorporating dazomet into the soil by mechanical means, it is fundamentally of prime advantage to be able to use dust-free granules.

A process for preparing such substantially dust-free granules is described in EP A 618 912. By adding alkylenediamines of the general formula $R^1NH—A—NHR$ (III) (R and $R^1$ independently are hydrogen or $C_1$–$C_4$-alkyl and A is a 1,2-ethylene, 1,3-propylene or 1,4-butylene bridge) in the course of dazomet's preparation, control is exerted over crystallization or granulation and so substantially dust-free dazomet granules are obtained with qualities advantageous to the end user. Corresponding products are obtainable commercially under the trade name Basamid from BASF Aktiengesellschaft.

Forest Prod. J. 43(2): 41–44 (1993), Acta Horticulture 382 (1995) p. 110 ff. and Food and Fiber Science, 27(2) 1995, pp. 183–197 and further references cited therein describe the use of dazomet granules and the mode of action of the released product methyl isothiocyanate

(II)

(MITC), which functions as the actual biologically active agent. Accordingly, dazomet itself can be regarded merely so to speak as a prodrug precursor.

Comparatively little is known even now about the nature and activation of the release of MITC from dazomet in the soil. The literature does, however, reveal that the soil pH, transition metals or, for example, soil moisture and soil temperature all have a part to play. This is confirmed by our own studies.

The dazomet granules prepared in accordance with the abovementioned EP 0 618 912, although being substantially dust-free, have but a very limited influence over the release of MITC and are therefore unable to provide a completely satisfactory solution to one application problem: the control of active substance release, and especially the retarding thereof.

Thus it has been found when using such dazomet granules that, given high soil temperatures of more than 30° C. and sufficient soil moisture, MITC is released very quickly and then when the granules are incorporated into the soil, especially in glasshouse applications, MITC may lead to temporary mucosae and eye irritations in the absence of proper ventilation and use.

It would therefore be desirable for this utility to retard the release of MITC to a sufficient degree to give the personnel charged with applying the product sufficient time to leave the glasshouse before the active substance is released.

An alternative soil decontaminant, gaseous methyl bromide, has disadvantages in terms of its known ozone harmfulness.

Metam fluid and metam-sodium are of only limited glasshouse utility owing to their very rapid and strong propensity to evolve gas, or even, as for example in California, are no longer approved.

The "Montreal Protocol on Substances that deplete the Ozone Layer" in Part IV: Assessment of the Economic Viability of Methyl Bromide Alternatives, April 1997 Report Vol. II cites on page 260 the use of dazomet as a potential alternative for methyl bromide but points to problems in its application by untrained users.

It is an object of the present invention to provide crop protection granules based on the active substance tetrahydro-3,5-dimethyl-3,5-thiadiazine-2-thione in which there is delayed and/or controlled release of the active substance.

We have found that this object is achieved by crop protection granules based on the active substance tetrahydro-3,5-dimethyl-1,3,5-thiadiazine-2-thione which comprise an outer shell which makes up from 0.1 to 50% by weight of the overall weight of the granules and of which at least 50% by weight consists of sulfur compounds or sulfur itself.

The subclaims and the subsequent description reveal preferred embodiments of the invention.

The invention additionally relates to a method of combating nematodes, soil-dwelling insects, germinating plants, soil bacteria and soil fungi by treating the soil with an effective amount of from 1 to 1000 kg/ha of soil surface of the granules of the invention.

The invention gives preference to dazomet granules as obtained by the process described in EP 618 912, i.e. to products in whose preparation from 0.1 to 10 mol % of diaminoalkylene compounds $R^1NH—A—NHR$ (R, $R^1$ and A are as defined at the outset) are added. For further preparation details reference is made to EP 618 912.

The outer shell preferably makes up from 1 to 35 and, in particular, from 2 to 25% by weight of the granules.

Preferably from 55 to 100 and, with particular preference, from 75 to 100% by weight of the shell consists of sulfur compounds or elemental sulfur.

A particularly preferred shell material is elemental sulfur, especially those products which can be employed in the form of aqueous dispersions.

Thus it has surprisingly been found that aqueous sulfur dispersions, such as aqueous redispersion concentrates of the commercial product Kumulus® DF, are particularly suitable as shell constituents.

An advantage of using such shell materials is that they can be applied to the dazomet granules by the fluidized bed technique without the occurrence of disadvantages in processing, such as agglomeration, formation of coarse grains or disadvantages in terms of the abrasion behavior.

Such sulfur dispersions are preferably prepared by one of the following techniques:

Technique A

Sulfur suspension concentrates by aqueous grinding techniques from elemental sulfur with appropriate auxiliaries Elemental sulfur, such as sulfur powder, is suspended in water, judiciously with the addition of wetting agents and dispersants and, if desired, with the addition of a binder. The still coarse sulfur suspension is then comminuted, preferably in plain or stirred ballmills with grinding media—for example, glass grinding media or other mineral or metallic grinding media—having a size (average diameter) of in general 0.1–30 mm, preferably 0.6–2 mm, until the average particle size is preferably less than 10 μm.

Technique B

Sulfur suspension concentrates from melt-spray sulfur granules redispersed in water Melt-spray sulfur granules are obtained by melting elemental sulfur, such as sulfur powder, by heating it to temperatures of more than 120° C. and spraying the resulting melt, directly or following the addition of wetting agents and dispersants, in an appropriate spraying device, such as in a spray tower, generally with cooling, to form the spray sulfur granules.

Examples of suitable wetting agents and dispersants for both techniques are the following auxiliaries from the following classes of substance:

Fatty acid polyoxyethylene esters, such as lauryl alcohol polyoxyethylene ether acetate, alkyl polyoxyethylene or polyoxypropylene ethers, such as those of isotridecyl alcohol, and fatty alcohol polyoxyethylene ethers, alkylaryl alcohol polyoxyethylene ethers, such as octylphenol-polyoxyethylene ether or tributylphenol polyoxyethylene ether, ethoxylated isooctyl-, octyl- or nonylphenol or castor oil, sorbitol esters, arylsulfonic acids, alkylsulfonic acids, alkylsulfuric acids or their alkali metal, alkaline earth metal and ammonium salts, especially salts of arylsulfonic acids, examples being lignin-, phenol-, naphthaline- and dibutylnaphthalinesulfonic acids, alkylsulfonic acids, alkylarylsulfonic acids, alkylsulfuric, lauryl ether sulfuric and fatty alcohol sulfuric acids, fatty acids, sulfated hexa-, hepta- and octadecanols and fatty alcohol glycol ethers, condensates of sulfonated naphthaline and its derivatives with formaldehyde, condensates of naphthalinesulfonic acids with phenol and formaldehyde, and protein hydrolysates.

In addition, lignin sulfite waste liquors and methylcellulose are also particularly suitable.

Examples which may be mentioned here are:

Benzenesulfonic acid and its $C_{10}$–$C_{16}$-alkylderivatives and also its sodium, potassium, calcium and magnesium salts, diisobutyl-,diisopropyl- and dimethylnaphthalinesulfonic acid and their corresponding sodium, potassium, calcium or magnesium salts, preferably the sodium salts, ammonium salts and sodium salts of the monoether of ethoxylated dodecanol with sulfuric acid, monoethers of ethoxylated dodecyl alcohol with sulfuric acid, various salts of dodecyl sulfate (Na, K, Ca, Mg), salts of dodecylbenzenesulfonic acid with Na, K, Ca, triethanolamine or triethylamine, ammonium or sodium salts of condensates of naphthalinesulfonic acid and formaldehyde, condensates of phenolsulfonic acid, urea and formaldehyde and salts thereof, xyloylsulfonic acid and its salts, and sodium salts of $C_{12}$–$C_{16}$ 2-alkenesulfonic acids.

The granules of the invention are preferably prepared in a fluidized bed unit. For this purpose the dazomet granules are then fluidized, and at the same time a generally aqueous sulfur dispersion (where such dispersions are used as shell materials), together if desired with further auxiliaries such as polymers, wetting agents or dispersants, emulsifiers or binders, is sprayed onto the granules of active substance.

Suitable auxiliaries and shell materials, which are sprayed onto the dazomet granules in mixtures, together or separately, with sulfur dispersions, include in particular the following binders: cellulose derivatives, such as cellulose esters, cellulose ethers carboxymethylcellulose, hydroxypropylmethylcellulose, water-soluble gums, such as gum arabic, gum tragacanth, alginates, gelatins, modified starches, such as sodium carboxymethyl starch, as auxiliaries from natural sources, and also cellulose, cellulose acetates, cellulose carboxymethyl ether and its sodium salt, cellulose 2-hydroxypropyl ether and cellulose 2-hydroxyethyl ether, cellulose ethyl ether, cellulose ethyl ether, and regenerated cellulose, to name but a few.

At least 50% by weight, preferably from 55 to 100% by weight, of the shell of the granules of the invention consists of sulfur or sulfur compounds. In order to control the properties of the shell, and in particular to control the release of MITC, it is also possible to use in addition to sulfur and sulfur compounds, for example, polymeric shell substances in an amount of up to 45% by weight, preferably up to 40% by weight, based on the shell.

It is preferred to employ aqueous wax dispersions comprising, based on the aqueous wax dispersion, from 5 to 40% by weight of an ethylene copolymer wax, consisting of from 10 to 25% by weight of an α-olefinically unsaturated mono- or dicarboxylic acid having 3 to 8 carbons and from 90 to 75% by weight of ethylene having an MFI, measured at 190° C. and under a load of 2.16 kp, of from 1 to 600, preferably from 5 to 500 and, in particular from 15 to 300, or having an MFI, measured at 160° C. and under 325 p, of from 1 to 600, from 0.1 to 5% by weight of alkali metal hydroxide, ammonia an alkanolamine or a dialkanolamine and mixtures thereof, and, as the remainder, water to 100%.

The copolymers of ethylene which are particularly suitable for wax dispersions contain from 10 to 25% by weight, preferably from 15 to 24% by weight, of α-olefinically unsaturated mono- or dicarboxylic acids having 3 to 8 carbons, of which examples that may be mentioned are acrylic, methacrylic, crotonic, maleic, fumaric and itaconic acid. Of these, methacrylic acid and especially acrylic acid and mixtures thereof are preferred.

The ethylene copolymer waxes are characterized by their MFI (Melt Flow Index) or melt index. The MFI indicates the amount of the polymer melt, in grams, which can be pressed through a nozzle of defined dimensions under a defined application of force (load) at a certain temperature. The melt indices (MFI units) are determined in accordance with the following standards: ASTM D 1238–65 T, ISO R 1133–1696 (E) or DIN 53 735 (1970).

In addition, the wax dispersions preferably comprise bases, generally 0.1–5, preferably from 1 to 3% by weight of alkali metal hydroxide, preferably sodium hydroxide or potassium hydroxide, ammonia, a mono-, di- or trialkanolamine having in each case 2 to 18 carbons in the hydroxyalkyl radical, preferably 2 to 6 carbons, or mixtures of said alkanolamines, or a dialkylmonoalkanolamine having in each case 2 to 8 carbons in the alkyl and hydroxyalkyl radicals, or mixtures thereof. Examples of amines are diethanolamine, triethanolamine, 2-amino-2-methyl-1-propanol or dimethylethanolamine. Ammonia is preferably used.

As a result of the base fraction in the wax dispersions, the carboxyl groups in the copolymer waxes are present at least in part in the salt form. Preferably, from 50 to 90% and, in particular, up to 60 to 85% of these groups are in neutralized form.

Particular preference is given to a wax dispersion which consists of or comprises from 5 to 40% by weight of an ethylene copolymer wax, from 0.1 to 5% by weight of ammonia and from 55 to 94.9% by weight of water, the ethylene copolymer wax being composed of from 75 to 90% by weight of ethylene units and up to from 10 to 25% by weight of units of an α-olefinically unsaturated mono- or dicarboxylic acid having 3 to 8 carbons.

Further examples of suitable polymeric shell materials are the following:
copolymers of butyl acrylate, 2-hydroxyethyl methacrylate, methacrylic acid and styrene,
copolymers of butyl acrylate, 2-hydroxyethyl methacrylate, methyl methacrylate and styrene,
copolymers of butyl acrylate, butyl methacrylate, methacrylic aid and styrene,
copolymers of butyl acrylate, hydroxyethyl acrylates and methylmethacrylate,
copolymers of butyl methacrylate, 2-ethylhexyl acrylate and styrene
copolymers of butyl methacrylate, 2-hydroxyethyl methacrylate, methyl methacrylate and styrene,
copolymers of n-butyl methacrylate, 2-hydroxyethyl methacrylate, methyl methacrylate and styrene,
ethylene-vinyl acetate copolymers,
sodium and ammonium salts of ethylene-acrylic acid copolymers,
copolymers of methyl methacrylate and acrylic acid, butyl acrylate, butyl methacrylate or mixtures thereof,
polyvinyl acetate, polyvinyl ethers, polyacrylamides, polyamides,
polyvinyl alcohol, polyvinylpyrrolidone,
polyvinylpyrrolidone-vinyl acetate copolymers,
copolymers of vinyl acetate with methyl acrylate, methyl methacrylate, butyl acrylate and acrylic acid or mixtures thereof, copolymers of vinylpyrrolidones with long-chain 1-alkenes, and copolymers of crotonic acid, vinyl acetate and vinyl propionate.

The shell layer may also comprise substances for controlling the release of the active substances. Examples are water-soluble substances such as polyethylene glycols, polyvinylpyrrolidone and copolymers of polyvinylpyrrolidone and polyvinyl acetate. The amount thereof is for example from 0.1 to 5% by weight, preferably from 0.1 to 3% by weight, based on the shell substance.

The above-described shell polymers are general knowledge or are obtainable by known methods (cf. e.g. DE-A 34 20 168; EP-A 201 702; U.S. Pat. No. 206 279).

Such shell layers are judiciously applied by spray application of solutions, dispersions or dispersion of said shell substances together with the sulfur or the sulfur compound in organic solvents or water.

It is preferred to use an aqueous suspension or an emulsion of the shell substance having, in particular, a content of polymer substance of from 0.1 to 50% by weight, in particular, from 1 to 35% by weight. In this case, further auxiliaries may also be added in order to optimize processing, examples being surfactants and solids such as talc and/or magnesium stearate.

The wax dispersions described above can also be applied together with sulfur dispersions and/or other auxiliaries to the dazomet granules by spray application in the fluidized bed technique.

With granules provided in accordance with the invention with an outer shell, MITC release is retarded significantly in comparison with the customary commercial products, especially at high temperatures, without a significant increase in the duration of the dissipation phase following treatment; in other words, the MITC mineralization required before resowing can begin takes place within virtually the same period of time as with the known products. This represents a significant technical advantage.

The crop protection granules of the invention may also include other active substances or may be applied together with other compositions together in unison, mixed or separately in succession. The proportion of the further active substances is preferably up to 20% by weight, in particular up to 10% by weight, based on the overall weight. Suitable further compositions are known per se to the skilled worker and are described in the literature, so that further details are unnecessary here.

EXAMPLES

Example 1

Preparing Melt-spray Sulfur Granules with Subsequent Redispersion in Water

Sulfur powder was heated to a temperature of more than 120° C. and melted. The melt was mixed with sodium ligninsulfonate as wetting agent and silica as dispersant. The melt mixture was sprayed in a spray tower using a dual-substance nozzle. This gave readily dispersible spray granules (particle diameter: $60<x<300\ \mu m$), containing 0.3% by weight of dispersant and about 20% by weight of wetting agent. The remainder was sulfur. The melt-spray granules obtained were then dispersed in an equal amount of water and the dispersion was then processed further in accordance with Example 3.

Example 2

Preparing a Sulfur Suspension by Aqueous-mechanical Fine Grinding in Stirred Mills Sulfur powder was suspended in water, and sodium ligninsulfonate is added as dispersant. Nonylphenol polyethoxylate was also added as a wetting agent. The suspension was adjusted to a pumpable concentration; a sulfur concentration of 50% by weight was judicious.

To form a sprayable suspension the batch was ground in a laboratory stirred mill until a particle distribution of 40%<2 micrometers was obtained.

Based on the total dry mass, the proportion of the sulfur was 80% by weight, the concentration of the sodium ligninsulfonate in the example was 19% by weight and that of the wetting agent was 1% by weight. The addition of an antifoam, such as silicone SRE in a concentration of up to 0.1%, suppressed the formation of foam in the course of milling.

compounds or volatile gases are generally found with dazomet breakdown. Calibration was done using a calibrating gas (propane in nitrogen) with account being taken of a substance-specific correction factor.

The results of the experiments are set out in Table 2 below.

TABLE 2

| Measurement period in h | Sample 1 Conc. MITC mg/m$^3$ | Sample 1 Conc. MITC mg/m$^3$ | Sample 1 Conc. MITC mg/m$^3$ | Sample 2 Conc. MITC mg/m$^3$ | Sample 3 Conc. MITC mg/m$^3$ | Sample 4 Conc. MITC mg/m$^3$ | Sample 5 Conc. MITC mg/m$^3$ |
|---|---|---|---|---|---|---|---|
| 0.5 | 110 | 361 | 550 | 220 | 110 | 110 | 220 |
| 1 | 220 | 723 | 1210 | 660 | 440 | 165 | 770 |
| 2 | 303 | 1627 | 3080 | 1980 | 1870 | 440 | 2420 |
| 6 | 743 | 3795 | 8030 | 4620 | 5060 | 1705 | 5940 |
| 12 | 1320 | 4389 | 5280 | 3740 | 4070 | 2585 | 4620 |
| 18 | 1678 | 3589 | 3080 | 2640 | 2640 | 2585 | 2915 |
| 24 | 1859 | 2556 | 1760 | 1760 | 1650 | 2145 | 1815 |
| Temp./°C. | 15 | 25 | 35 | 35 | 35 | 35 | 35 |

Example 3

Preparing the Dazomet Granules of the Invention 2 kg of granules prepared in accordance with EP 0 618 912 were introduced into a spray fluidized bed.

A 50% aqueous suspension of sulfur was then sprayed onto these carrier granules in the course of 20 minutes. The dazomet granules during this time were fluidized with an air quantity of 130 m$^3$/h. The aqueous sulfur suspension is sprayed on at a pressure of 1.5 bar.

The following samples were prepared by the method described above:

TABLE 1

| Sample No. | Proportion by weight of the outer shell and its composition |
|---|---|
| 1 | no shell (control sample) |
| 2 | 10% of S granules as in Ex. 3 |
| 3 | 20% of S-granules as in Ex. 3 |
| 4 | 10% of S-granules as in Ex. 3 + 5% of polymer 1 |
| 5 | 5% of S granules as in Ex. 3 + 5% of polymer 2 |

The polymer 1 employed in sample 4 is a wax dispersion in accordance with Example 1 of EP 734,205; the polymer 2 employed in sample 5 was sodium salt of a phenolsulfonic acid/formaldehyde/urea condensate.

MITC release was determined by the following method: 400 g of dried and non-lumpy soil (pH 7.9 Limburgerhof site) were mixed thoroughly with 160 mg of samples 1 to 5, wetted with 50 ml of water and placed in a test vessel (glass, internal diameter of 100 mm, gas space 300 ml), which was then sealed and placed in a climatically controlled cabinet. 10 ml/min of purified air were passed through the vessel. On leaving the vessel, this air was passed directly through a heated connecting line into the flame ionization detector (FID) of a gas chromatograph. The detector signal corresponds virtually 100% to the organic carbon content of the measured gas. Other than methyl isocyanate, virtually no further FID-detectable The results of the experiments carried out show that in all cases the envelopment in a shell achieves a significantly retarded release of MITC at 35° C. The rate of release corresponds approximately to that of the granules without a shell at 15° C. It is advantageous and surprising, especially in the case of sample 4, that just 6 h after incorporation—this corresponds roughly to practice—a higher rate of release is obtained than in the case of granules without a shell at 15° C. This is a desirable effect, since a faster rate of MITC dissipation is achieved thereby, despite the initially delayed release, and hence an earlier resowing date is possible in the case of new planting.

A further positive effect is that at the application rates of the dazomet granules, which lie preferably within the range from 1 to 1000 kg/ha, with particular preference from 10 to 800 and, in particular, from 100 to 600 kg/ha of soil surface, significant amounts of sulfur are introduced into the soil, which by virtue of fertilization effects are to the long-term good of the plant growth.

Moreover, an additional fungicidal, nematicidal or insecticidal effect is anticipated by virtue of the sulfur.

What is claimed is:

1. Crop protection granules comprising a core of tetrahydro-3,5-dimethyl-1,3,5-thiadiazine-2-thione as an active substance and an outer shell, the proportion of the outer shell being from 0.1 to 50% by weight, based on the weight of the entire granules, wherein at least 50% by weight of the shell consists of elemental sulfur.

2. The crop protection granules of claim 1, wherein sulfur in the form of a suspension concentrate is the starting material for the outer shell.

3. The crop protection granules of claim 1, wherein the active substance present has been prepared with the addition of from 0.1 to 10 mol % of diaminoalkylene compounds of formula III $$R^1NH-A-NHR \quad (III)$$

where R and $R^1$ independently are hydrogen or a $C_1$–$C_4$-alkyl group and A is a 1,2-ethylene, 1,3-propylene or 1,4-butylene bridge.

4. A method of combating nematodes, soil-dwelling insects, germinating plants, soil bacteria and soil fungi, which comprises treating the soil with an amount of from 1 to 1000 kg/ha of soil surface of the crop protection granules of claim 1.

5. A process for preparing crop protection granules as defined in claim 1, which comprises (a) fluidizing granules of the active substance tetrahydro-3,5-dimethyl-1,3,5-thiadiazine-2-thione by a fluidized ed technique and (b) coating the fluidized granules from (a) with an aqueous suspension of the shell material.

6. Crop protection granules as claimed in claim 1, wherein from 55 to 100% of the outer shell is elemental sulfur.

7. Crop protection granules as claimed in claim 1, wherein from 75 to 100% of the outer shell is elemental sulfur.

8. Crop protection granules as claimed in claim 1, wherein the outer shell constitutes from 1 to 35% by weight of the granules.

9. Crop protection granules as claimed in claim 1, wherein the outer shell constitutes from 2 to 25% by weight of the granules.

\* \* \* \* \*

UNITED STATES PATENT AND TRADEMARK OFFICE
CERTIFICATE OF CORRECTION

PATENT NO. : 6,410,042 B1
DATED : June 25, 2002
INVENTOR(S) : Schroeder et al.

It is certified that error appears in the above-identified patent and that said Letters Patent is hereby corrected as shown below:

Column 9,
Line 14, "ed" should be -- bed --.

Signed and Sealed this

Fifteenth Day of October, 2002

Attest:

JAMES E. ROGAN
Attesting Officer  Director of the United States Patent and Trademark Office